(12) United States Patent
Liu et al.

(10) Patent No.: US 10,898,733 B2
(45) Date of Patent: *Jan. 26, 2021

(54) BEAM SHAPING ASSEMBLY FOR NEUTRON CAPTURE THERAPY

(71) Applicant: NEUBORON MEDTECH LTD., Jiangsu (CN)

(72) Inventors: Yuan-Hao Liu, Jiangsu (CN); Wei-Lin Chen, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 428 days.

This patent is subject to a terminal disclaimer.

(21) Appl. No.: 15/918,262

(22) Filed: Mar. 12, 2018

(65) Prior Publication Data

US 2018/0193673 A1 Jul. 12, 2018

Related U.S. Application Data

(63) Continuation of application No. PCT/CN2016/089731, filed on Jul. 12, 2016.

(30) Foreign Application Priority Data

Sep. 30, 2015 (CN) .......................... 2015 1 0643065
Sep. 30, 2015 (CN) ..................... 2015 2 0770873 U

(51) Int. Cl.
*A61N 5/10* (2006.01)

(52) U.S. Cl.
CPC ............ *A61N 5/1081* (2013.01); *A61N 5/10* (2013.01); *A61N 2005/109* (2013.01); *A61N 2005/1095* (2013.01); *A61N 2005/1098* (2013.01)

(58) Field of Classification Search
CPC .. A61N 5/1081; A61N 5/10; A61N 2005/109; A61N 2005/1095; A61N 2005/1098; H05H 3/06; H05H 6/00
(Continued)

(56) References Cited

U.S. PATENT DOCUMENTS 9,889,320 B2 * 2/2018 Liu .......................... H05H 6/00
9,974,979 B2 * 5/2018 Liu ....................... A61N 5/1077
(Continued)

FOREIGN PATENT DOCUMENTS

CN 200998534 Y 1/2008
CN 103052425 A 4/2013
(Continued)

OTHER PUBLICATIONS

International Search Report of PCT/CN2016/089731, dated Sep. 27, 2016.

*Primary Examiner* — Nicole M Ippolito
(74) *Attorney, Agent, or Firm* — Locke Lord LLP; Tim Tingkang Xia, Esq.

(57) ABSTRACT

A beam shaping assembly for neutron capture therapy includes a beam inlet, a target having nuclear reaction with an incident proton beam from the beam inlet to produce neutrons forming a neutron beam, a moderator adjoining to the target, a reflector surrounding the moderator. The neutrons are moderated to epithermal neutron energies by the moderator, and part of the moderator disposed on the back of the target can be replaced so as to adjust the epithermal neutron energies. The reflector leads the neutrons deviated from the main axis back.

20 Claims, 3 Drawing Sheets

(58) Field of Classification Search
USPC .......................................... 250/492.1, 492.3
See application file for complete search history.

(56) References Cited

U.S. PATENT DOCUMENTS

| | | | |
|---|---|---|---|
| 10,124,192 B2* | 11/2018 | Liu | .......................... H05H 6/00 |
| 10,328,286 B2* | 6/2019 | Liu | ...................... A61N 5/1042 |
| 10,434,333 B2* | 10/2019 | Liu | .......................... A61N 5/10 |
| 10,610,704 B2* | 4/2020 | Liu | .......................... G21G 4/02 |
| 10,617,893 B2* | 4/2020 | Liu | ...................... C04B 35/645 |
| 10,639,499 B2* | 5/2020 | Liu | ........................ G21K 1/067 |
| 2007/0252093 A1 | 11/2007 | Fujimaki et al. | |
| 2018/0243587 A1* | 8/2018 | Liu | .......................... A61N 5/10 |

FOREIGN PATENT DOCUMENTS

| | | |
|---|---|---|
| CN | 104511096 A | 4/2015 |
| CN | 104575653 A | 4/2015 |
| CN | 205073543 U | 3/2016 |
| JP | 2008022920 A | 2/2008 |
| JP | 2014115122 A | 6/2014 |

* cited by examiner

BEAM SHAPING ASSEMBLY FOR NEUTRON CAPTURE THERAPY

RELATED APPLICATION INFORMATION

This application is a continuation of International Application No. PCT/CN2016/089731, filed on Jul. 12, 2016, which claims priority to Chinese Patent Application No. 201510643065.2, filed on Sep. 30, 2015; Chinese Patent Application No. 201520770873.0, filed on Sep. 30, 2015, the disclosures of which are hereby incorporated by reference.

FIELD OF THE DISCLOSURE

The present disclosure relates generally to a beam shaping assembly, and, more particularly, to a beam shaping assembly for neutron capture therapy.

BACKGROUND OF THE DISCLOSURE

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

BNCT takes advantage that the boron ($^{10}$B)-containing pharmaceuticals have high neutron capture cross section and produces $^4$He and $^7$Li heavy charged particles through $^{10}$B(n,α)$^7$Li neutron capture and nuclear fission reaction. As illustrated in FIG. 1, a schematic view of boron neutron capture reaction are shown, the two charged particles, with average energy at about 2.33 MeV, are of linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. When the boronated pharmaceuticals are gathered in the tumor cells selectively, only the tumor cells will be destroyed locally with a proper neutron source on the premise of having no major normal tissue damage.

BNCT is also well known for binary cancer therapy, for its effectiveness depending on the concentration of the boronated pharmaceuticals and the number of the thermal neutrons at the tumor site. Thus, besides development of the boronated pharmaceuticals, improvement of flux and quality of the neutron source plays a significant role in BNCT researches.

However, a beam shaping assembly for boron neutron capture therapy in the prior art is often designed to be of an integral fixed structure. The spectrum of the neutron beam output by such a beam shaping assembly is often constant, but in an actual therapy process, requirements for the neutron beam spectrum are not monotonous. For different patients, tumors may be different in terms of position, depth and type, which may result in different requirements for the neutron beam spectrum in a therapy process. The beam shaping assembly with the integral structure in the prior art cannot adjust the neutron beam spectrum according to a specific condition of a tumor in a patient to perform therapy under an actual condition of the patient.

Therefore, it is really necessary to provide a new technical solution so as to solve the foregoing problem.

The statements in this section merely provide background information related to the present disclosure and may not constitute prior art.

SUMMARY

In order to satisfy the accuracy of the neutron beam quality, an aspect of the present disclosure provides a beam shaping assembly for neutron capture therapy includes: a beam inlet; a target, wherein the target has nuclear reaction with the incident proton beam from the beam inlet to produce neutrons; a moderator adjoining to the target, wherein the neutrons are moderated by the moderator to epithermal neutron energies and the moderator is replaceable so as to adjust the epithermal neutron energies; a reflector surrounding the moderator leads the deflected neutrons back to enhance the epithermal neutron beam intensity; and a beam outlet.

Implementations of this aspect may include one or more of the following features.

The moderator includes a base portion disposed on the back of the target and an expanding portion separated from the base portion, wherein the expanding portion is replaceable independently to adjust the epithermal neutron energies.

More particularly, the base portion adjoins to the back of the target and is fixed to the target, and the expanding portion is arranged at the back of the base portion and adjoins to the base portion.

More particularly, the expanding portion at least includes a first expanding portion adjoins the base portion and a second expanding portion is arranged on the back of first expanding portion and adjoining to the first expanding portion, and at least one of the first expanding portion and the second expanding portion is replaceable independently.

More particularly, the reflector at least includes a supplementary reflecting portion surrounding the expanding portion.

More particularly, both of the supplementary reflecting portion and the expanding portion are replaceable to adjust the epithermal neutron energies.

More particularly, the supplementary reflecting portion and the expanding portion are moved into the beam shaping assembly through a guide slot arranged on the reflector to adjust the epithermal neutron energies.

More particularly, the supplementary reflecting portion and the reflector surrounding the base portion co-reflect deflected neutrons.

Further, the reflector is provided with a guide slot for guiding the expanding portion into the beam shaping assembly and the guide slot is extending to the back of the base portion, the guide slot is provided with a slide rail, the expanding portion is amounted in the guide slot and moves along the slide rail, so as to adjoin to the back of the base portion; the guide slot at least includes a first guide slot corresponding to the first expanding portion and a second guide slot corresponding to the second expanding portion; when the first expanding portion and the second expanding portion are identical in structure size and different in material, the first expanding portion and the second expanding portion are installed in the first guide slot or the second guide slot respectively; and when the first expanding portion and the second expanding portion are different in structure size and different in material, the first expanding portion is installed in the first guide slot, and the second expanding portion is installed in the second guide slot.

More particularly, the materials of the base portion, the first expanding portion and the second expanding portion is made of at least one of Al, Pb, Ti, Bi, C, $D_2O$, $AlF_3$, $CaF_2$, $Li_2CO_3$, $MgF_2$ and $Al_2O_3$, the reflector is made of at least one of Pb or Ni.

In another aspect of the present disclosure, a beam shaping assembly for neutron capture therapy is provided for satisfying the accuracy of the neutron beam quality. The beam shaping assembly includes a beam inlet; a target, wherein the target has nuclear reaction with an incident proton beam from the beam inlet to produce neutrons, and the neutrons form a neutron beam; a moderator adjoins to the target, wherein the neutrons are moderated by the moderator to epithermal neutron energies, and the moderator defines a base portion and an expanding portion, the base portion is fixed to the target and the expanding portion adjoins to the base portion, the expanding portion is replaceable independently; a reflector surrounds the moderator, wherein the reflector leads deflected neutrons back to enhance the epithermal neutron beam intensity; and a beam outlet.

Further, the expanding portion at least includes a first expanding portion disposed at the back of the base portion and adjoining to the base portion and a second expanding portion arranged at the back of the first expanding portion and adjoining to the first expanding portion, and at least one of the first expanding portion and the second expanding portion is replaceable independently.

More particularly, the reflector at least includes a supplementary reflecting portion surrounding the expanding portion.

Further, both of the supplementary reflecting portion and the expanding portion are replaceable to adjust the epithermal neutron energies.

More particularly, the supplementary reflecting portion and the expanding portion are moved into the beam shaping assembly through a guide slot arranged on the reflector to adjust the epithermal neutron energies.

Further, the supplementary reflecting and the reflector surrounding the base portion co-reflect deflected neutrons.

In yet another aspect of the present disclosure, a beam shaping assembly for neutron capture therapy is provided for satisfying the accuracy of the neutron beam quality. The beam shaping assembly for neutron capture therapy includes a beam inlet; a target, wherein the target has nuclear reaction with an incident proton beam from the beam inlet to produce neutrons; a moderator adjoining to the target, wherein the neutrons are moderated by the moderator to epithermal neutron energies, the moderator includes at least a expanding portion, the expanding portion is replaceable independently without changing the whole moderator; and a reflector surrounding the moderator, wherein the reflector leads the deflected neutrons back to enhance the epithermal neutron beam intensity; a beam outlet.

Further, the expanding portion at least includes a first expanding portion adjoining to the target and a second expanding portion arranged at the back of the first expanding portion and adjoining to the first expanding portion, and at least one of the first expanding portion and the second expanding portion is replaceable independently.

Further, the moderator includes a base portion fixed to the target, and the first expending portion is disposed on the back of the base portion.

More particularly, the expanding portion can be made of at least one of Al, Pb, Ti, Bi, C, $D_2O$, $AlF_3$, $CaF_2$, $Li_2CO_3$, $MgF_2$ and $Al_2O_3$.

Further areas of applicability will become apparent from the description provided herein. It should be understood that the description and specific examples are intended for purposes of illustration only and are not intended to limit the scope of the present disclosure.

DETAILED DESCRIPTION

Figure 1:
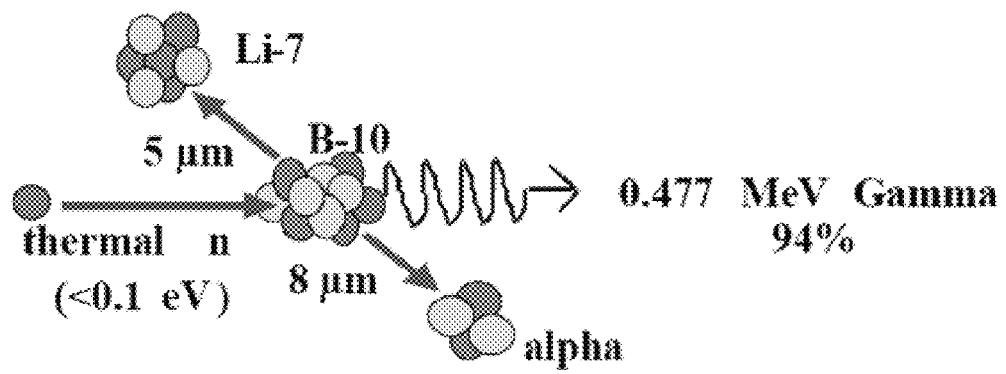
FIG. 1 is a schematic view of boron neutron capture reaction.

The following description of the preferred embodiments is merely exemplary in nature and is in no way intended to limit the invention, its application, or uses.

Neutron capture therapy (NCT) has been increasingly practiced as an effective cancer curing means in recent years, and BNCT is the most common. Neutrons for NCT may be supplied by nuclear reactors or accelerators. Take AB-BNCT for example, its principal components include, in general, an accelerator for accelerating charged particles (such as protons and deuterons), a target, a heat removal system and a beam shaping assembly. The accelerated charged particles interact with the metal target to produce the neutrons, and suitable nuclear reactions are always determined according to such characteristics as desired neutron yield and energy, available accelerated charged particle energy and current and materialization of the metal target, among which the most discussed two are $^7Li\ (p, n)\ ^7Be$ and $^9Be\ (p, n)^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions.

The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. The target in these embodiments of the present disclosure is made of lithium. However, well known by those skilled in the art, the target materials may be made of other metals besides the above-mentioned.

Requirements for the heat removal system differ as the selected nuclear reactions. $^7$Li (p, n) $^7$Be asks for more than $^9$Be (p, n)$^9$B does because of low melting point and poor thermal conductivity coefficient of the metal (lithium) target. In these embodiments of the present disclosure is $^7$Li (p, n)$^7$Be.

Especially, during the actual neutron capture therapy, specific conditions (such as the tumor position, the depth of the tumor and the type of the tumor) of tumors of different patients may be different. Therefore, specific requirements (such as specific ranges of beam neutron energies region, neutron beam flux or even forward directional characteristics of neutron beams) for neutron beam quality generated after a nuclear reaction between protons and a target may be different. In order to enable the neutron capture therapy technology to be applied to an actual therapy process for a tumor patient more flexibly and more accurately, or even applied to more kinds of tumor therapy, the present application improves a beam shaping assembly for neutron capture therapy. Preferably, the improvement aims to a beam shaping assembly for an accelerator boron neutron capture therapy.

Figure 2:
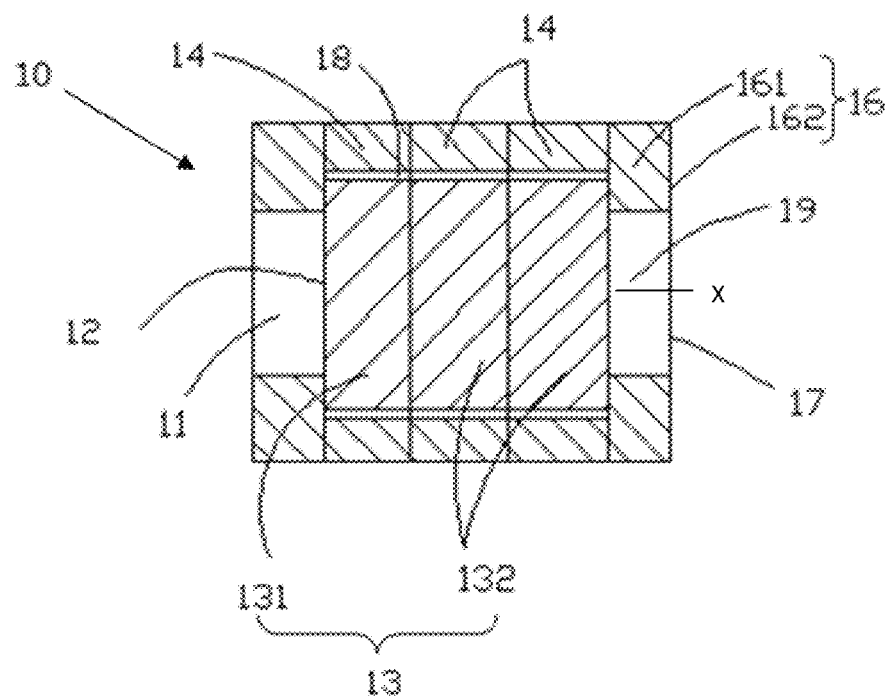
FIG. 2 is a schematic view of the beam shaping assembly for neutron capture therapy in the first embodiment of the present disclosure, wherein an expanding portion is installed through a guide slot.
Figure 3:
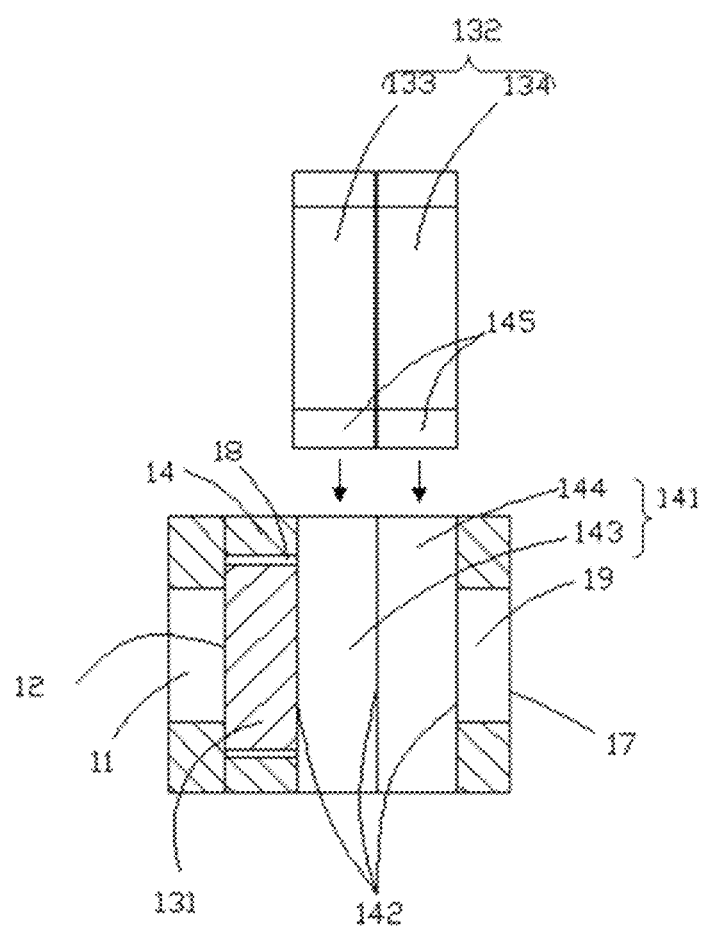
FIG. 3 is another schematic view of the beam shaping assembly for neutron capture therapy in the first embodiment, wherein the expanding portion has not been arranged into the guide slot.
Figure 4:
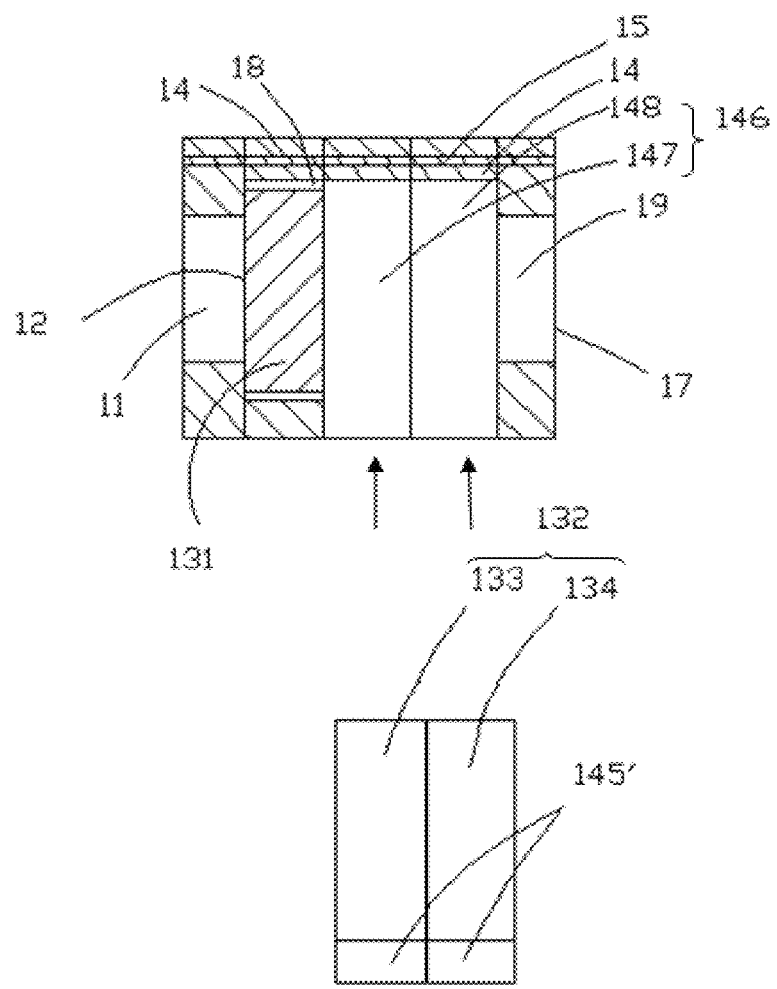
FIG. 4 is a schematic view of the beam shaping assembly for neutron capture therapy in the second embodiment of the present disclosure, wherein an expanding portion is installed by using a rotary table.

FIG. 2 to FIG. 4 show a beam shaping assembly 10 for neutron capture therapy in the present application. The beam shaping assembly 10 includes a beam inlet 11, a target 12, a moderator 13 adjoining to the target 12, a reflector 14 surrounding the moderator 13, and a beam outlet 17. The proton beam is accelerated by an accelerator, the energy of the proton beam is accelerated to be high enough to overcome energy of nuclear forces of the target, the target 12 has nuclear reaction ($^7$Li(p,n)$^7$Be nuclear reaction, referring to FIG. 1) with the proton beam incidence from the beam inlet 11 to produce neutrons; The neutrons form a neutron beam, the neutron beam defines a axis. The generated neutrons are moderatored by the moderated 13, and deflected neutrons are reflected back to the beam axis by the reflector 14 and then emit out of the beam outlet 17.

The moderator 13 can be made of various materials, the material of the moderator 13 greatly affects these indexes such as beam neutron energy region, neutron beam flux or even forward directional characteristics of a neutron beam. In the present application, the moderator 13 is replaceable, so as to solve the situation where the same medical equipment cannot be used for performing neutron capture therapy under different tumor conditions (including position, depth and type).

The moderator 13 includes a base portion 131 and an expanding portion 132, the base portion 131 and the expanding portion 132 are separable. The base portion 131 is located at the back of the target 12, and the expanding portion 132 is installed at the back of the base portion 131. The expanding portion 132 is replaceable, and the base portion 131 can be arranged to be replaceable or fixed. When the base portion 131 is replaceable, the base portion 131 and the expanding portion 132 is replaceable respectively; and when the base portion 131 is fixed, only the expanding portion 132 is replaceable. Absolutely, the base portion 131 and the expanding portion 132 can also be arranged to be integral. For different tumor conditions, the whole moderator 13 is replaced to change the moderator capability of the moderator 13.

In the present embodiment, the base portion 131 and expanding portion 132 are designed as a separable structure, and the base portion 131 is fixed. The base portion 131 of the moderator 13 is disposed at the back of the target 12 and adjoins to the target 12 fixedly, and the expanding portion 132 is installed on the back of the base portion 131 and adjoins to the base portion 131 (in other embodiments, the expanding portion 132 cannot adjoin to the base portion 131, and a gap is formed between the base portion 131 and the expanding portion 132). In this embodiment, the expanding portion 132 at least includes a first expanding portion 133 and a second expanding portion 134. The first expanding portion 133 adjoins to the back of the base portion 131, and the second expanding portion 134 adjoins to the first expanding portion 133, so the expanding portion 132 forms lamination of two structures, and at least one of the first expanding portion 133 and the second expanding portion 134 can be replaced independently. It is important to note that the expanding portion 132 may be laminated by two or more (three, four, five or more) structures due to various materials of moderator 13, so as to more finely change the moderating capability of the moderator 13 to meet the accuracy of the neutron beam quality, thereby enhancing the therapy effect on different tumors.

How to replace the expanding portion 132 of the moderator 13 will be specifically introduced hereinbelow.

Please refer to FIG. 3 again. FIG. 3 is a schematic view of the beam shaping assembly for neutron capture therapy in the first embodiment of the present application. In the first embodiment, a guide slot 141 is provided on the reflector 14, a slide rail 142 is disposed in the guide slot 141, and the expanding portion 132 is installed in the guide slot 141, and moves to the back of the base portion 131 along the slide rail 142, and adjoins to the base portion 131. The guide slot 141 at least includes a first guide slot 143 and a second guide slot 144. When the structure of the whole moderator 13 is a cylinder, the first expanding portion 133 and the second expanding portion 134 are identical in structure size, only need to select the first expanding portion 133 and the second expanding portion 134 made of appropriate materials to install in the first guide slot 143 and the second guide slot 144 respectively according to the requirements for neutron beam quality. That is to say, in this case, since the first expanding portion 133 and the second expanding portion 134 are identical in structure size, only need to ensured that the material of the expanding portion 132 installed in the first guide slot 143 and the second guide slot 144 can meet the requirements of the expected neutron beam quality after passing through the moderator 13, and without limits to whether the first expanding portion 133 or the second expanding portion 134 is installed in the first guide slot 143 and the second guide slot 144. When the structure of the whole moderator 13 is a cylinder or a cone or a combination of a cylinder and a cone and the first expanding portion 133 and the second expanding portion 134 are different in structure size, the first expanding portion 133 and the second expanding portion 134 made of different materials are selected according to the requirements of the expected neutron beam quality, the first expanding portion 133 can only be installed in the first guide slot 143, and the second expanding portion 134 can only be installed in the second guide slot 144.

The reflector 14 further includes supplementary reflecting portion 145 disposed on two outer sides of the expanding portion 132 and installed in the guide slot 141. The supplementary reflecting portion 145 can be integrated with the expanding portion 132 and installed in the guide slot 141 along with the expanding portion 132, or can be installed in the guide slot 141 independently after the expanding portion 132 is installed in the guide slot 141. When the expanding portion 132 is installed at the back of the base portion 131 through the slide rail 142, the supplementary reflectors 145 and the reflector 14 surrounding the base portion 131 co-reflect deflected neutrons, such that the deflected neutrons are reflected back to a main axis of the neutron beam to improve the beam strengths of the epithermal neutrons.

Please refer to FIG. 4 again. FIG. 4 is a schematic view of the beam shaping assembly for neutron capture therapy in the second embodiment of the present application. In the second embodiment, components identical to those in the first embodiment are marked by the same digits identical to those in the first embodiment. In the second embodiment, a rotary shaft 15 parallel to a central line of the base portion 131 of the moderator 13 is disposed on the reflector 14, and the rotary shaft 15 is provided with a rotary table 146 which is located on the back of the base portion 131 and can rotate relative to the base portion 131. The expanding portion 132 is installed in the rotary table 146, rotates to the back of the base portion 131 around the rotary shaft 15 along with the rotary table 146, and adjoins to the base portion 131. The rotary table 146 at least includes a first rotary table 147 and a second rotary table 148. When the structure of the whole moderator 13 is a cylinder and the first expanding portion 133 and the second expanding portion 134 are identical in structure size, select the first expanding portion 133 and the second expanding portion 134 made of appropriate materials to installed in the first rotary table 147 or the second rotary table 148. In this case, since the first expanding portion 133 and the second expanding portion 134 are identical in structure size, only need to ensured that the material of the expanding portion 132 installed in the first rotary table 147 and the second rotary table 148 can meet the requirements of the expected neutron beam quality after passing through the moderator 13, and without limits to whether the first expanding portion 133 or the second expanding portion 134 is installed in the first rotary table 147 and the second rotary table 148. When the structure of the whole moderator 13 is a cylinder or a cone or a combination of a cylinder and a cone and the first expanding portion 133 and the second expanding portion 134 are different in structure size, the first expanding portion 133 and the second expanding portion 134 made of different materials are selected according to the requirements of the expected neutron beam quality, the first expanding portion 133 can only be installed in the first rotary table 147, and the second expanding portion 134 can also only be installed in the second rotary table 148.

The reflector 14 further includes supplementary reflecting portion 145' disposed on the outer sides of the expanding portion 132, and the supplementary reflecting portion 145' can be integrated with the expanding portion 132 and installed in the rotary table 146 along with the expanding portion 132, and also can be installed in the rotary table 146 independently after the expanding portion 132 is installed in the rotary table 146. When the expanding portion 132 is installed at the back of the base portion 131 in a manner of rotating around a rotary shaft 15, the supplementary reflectors 145' and the reflector 14 surrounding the base portion 131 co-reflect deflected neutrons, such that the deflected neutrons are reflected back to a main axis of the neutron beam to improve the beam strengths of the epithermal neutrons.

The materials of the moderator 13 are of a large fast neutron action cross-section and a small epithermal neutron action cross-section. Preferably, the moderator 13 is made of at least one of Al, Pb, Ti, Bi, C, $D_2O$, $AlF_3$, Fluental™, $CaF_2$, $Li_2CO_3$, $MgF_2$ and $Al_2O_3$. Further, the base portion 131 of the moderator 13 is made of at least one of Al, Pb, Ti, Bi, C, $D_2O$, $AlF_3$, Fluental™, $CaF_2$, $Li_2CO_3$, $MgF_2$ and $Al_2O_3$. The material of the first expanding portion 133 and the second expanding portion 134 are also made of at least one of Al, Pb, Ti, Bi, C, $D_2O$, $AlF_3$, Fluental™, $CaF_2$, $Li_2CO_3$, $MgF_2$ and $Al_2O_3$. That is to say, the materials of the first expanding portion 133, the second expanding portion 134 and the base portion 131 in this application can be made of consistent or different materials. The materials of the reflector 14 are of strong neutron reflection ability. As a preferable embodiment, the reflector 14 is made of at least one of Pb or Ni.

In addition, a thermal neutron absorber (not shown in the figure) is disposed adjacent to the moderator 13, a gap passage 18 is disposed between the moderator 13 and the reflector 14, an air passage 19 is disposed between the thermal neutron absorber and the beam exit 17, and a radiation shield 16 capable of reducing the normal tissue dose of a non-radiation region is disposed in the reflector 14. The gap passage 18 refers to an empty region which is not covered by a solid material and is easily passed by a neutron beam, and the gap passage 18 is an air channel or a vacuum channel. The flux of the epithermal neutrons can be increased by the gap passage 18, and neutrons deflected from the main axis of the neutron beam can be continuously guided back to the main axis by the air passage 19 so as to improve the beam strengths of the epithermal neutrons. The radiation shield 16 includes a photon shield 161 for shielding leaked photons in the neutron beam and a neutron shield 162 for shielding leaked neutrons in the neutron beam. The photon shield 161 and the reflector 14 can be integrated or can be split, and the neutron shield 162 is close to the beam exit 17.

The target 12 has nuclear reaction with an incident proton beam from the beam inlet 11 to produce neutrons, the neutrons form a neutron beam, the neutron beam defines a beam main axis, and the neutrons are moderated by moderator 13 to epithermal neutron energies, the thermal neutron absorber absorbs thermal neutrons in the neutron beam to avoid too much dose caused by superficial normal tissues during therapy, and the reflector 14 guides the neutrons deflected from the beam main axis back to the beam main axis to improve the beam strengths of the epithermal neutrons, so as to obtain beam quality most satisfying therapy on the patient.

The thermal neutron absorber is made of a material having a large thermal neutron action cross-section. As a preferable embodiment, the thermal neutron absorber is made of $^6$Li. Preferably, the material of the photon shield 161 is made of Pb, and the material of the neutron shield is made of polyethylene (PE). It is well-known to a person skilled in the art that the photon shield 161 can be made of other materials to make it capable of shielding photons, and the neutron shield 162 can also be made of other materials or disposed at other places to make it capable of satisfying conditions of shielding leaked neutrons.

The beam shaping assembly for neutron capture therapy in this application only needs to select the moderator made of different material to adjust the moderating ability according to actual requirements of tumors for indexes such as a beam neutron energy and neutron beam flux, so different patients can be treated by using the same medical equipment with different energies of neutrons. The beam shaping assembly in this application has a simple structure and is high in applicability.

The above illustrates and describes basic principles, main features and advantages of the present disclosure. Those skilled in the art should appreciate that the above embodiments do not limit the present disclosure in any form. Technical solutions obtained by equivalent substitution or equivalent variations all fall within the scope of the present disclosure.

What is claimed is:

1. A beam shaping assembly for neutron capture therapy comprising:
    a beam inlet;
    a target, wherein the target has nuclear reaction with the incident proton beam from the beam inlet to produce neutrons;
    a moderator adjoining to the target, wherein the neutrons are moderated by the moderator to epithermal neutron energies and the moderator is replaceable so as to adjust the epithermal neutron energies;
    a reflector surrounding the moderator, wherein the reflector leads deflected neutrons back to enhance the epithermal neutron beam intensity; and
    a beam outlet.

2. The beam shaping assembly for neutron capture therapy according to claim 1, wherein the moderator comprises a base portion disposed on the back of the target and an expanding portion separated from the base portion, and wherein the expanding portion is replaceable independently to adjust the epithermal neutron energies.

3. The beam shaping assembly for neutron capture therapy according to claim 2, wherein the base portion adjoins to the back of the target and is fixed to the target, and the expanding portion is arranged at the back of the base portion and adjoins to the base portion.

4. The beam shaping assembly for neutron capture therapy according to claim 2, wherein the expanding portion at least comprises a first expanding portion disposed on the back of the base portion and adjoining to the base portion and a second expanding portion arranged at the back of the first expanding portion and adjoining to the first expanding portion, and at least one of the first expanding portion and the second expanding portion is replaceable independently.

5. The beam shaping assembly for neutron capture therapy according to claim 2, wherein the reflector at least comprises a supplementary reflecting portion surrounding the expanding portion.

6. The beam shaping assembly for neutron capture therapy according to claim 5, wherein both of the supplementary reflecting portion and the expanding portion are replaceable to adjust the epithermal neutron energies.

7. The beam shaping assembly for neutron capture therapy according to claim 6, wherein the supplementary reflecting portion and the expanding portion are moved into the beam shaping assembly through a guide slot arranged on the reflector to adjust the epithermal neutron energies.

8. The beam shaping assembly for neutron capture therapy according to claim 6, wherein the supplementary reflecting portion and the reflector surrounding the base portion co-reflect deflected neutrons.

9. The beam shaping assembly for neutron capture therapy according to claim 4, wherein the reflector is provided with a guide slot for guiding the expanding portion into the beam shaping assembly and the guide slot is extending to the back of the base portion, the guide slot is provided with a slide rail, the expanding portion is amounted in the guide slot and moves along the slide rail, so as to adjoin to the back of the base portion; the guide slot at least comprises a first guide slot a second guide slot; when the first expanding portion and the second expanding portion are identical in structure size and different in material, the first expanding portion and the second expanding portion are installed in the first guide slot or the second guide slot respectively; and when the first expanding portion and the second expanding portion are different in structure size and different in material, the first expanding portion is installed in the first guide slot, and the second expanding portion is installed in the second guide slot.

10. The beam shaping assembly for neutron capture therapy according to claim 4, wherein the materials of the base portion, the first expanding portion and the second expanding portion are made of at least one of Al, Pb, Ti, Bi, C, $D_2O$, $AlF_3$, $CaF_2$, $Li_2CO_3$, $MgF_2$ and $Al_2O_3$, the reflector is made of at least one of Pb or Ni.

11. A beam shaping assembly for neutron capture therapy comprising:
    a beam inlet;
    a target, wherein the target has nuclear reaction with an incident proton beam from the beam inlet to produce neutrons;
    a moderator adjoining to the target, wherein the neutrons are moderated by the moderator to epithermal neutron energies, and the moderator comprises a base portion fixed to the target and an expanding portion adjoining to the base portion, one of the base portion and the expanding portion is replaceable independently;
    a reflector surrounding the moderator, wherein the reflector leads deflected neutrons back to enhance epithermal neutron beam intensity; and
    a beam outlet.

12. The beam shaping assembly for neutron capture therapy according to claim 11, wherein the expanding portion at least comprises a first expanding portion disposed on the back of the base portion and adjoining to the base portion and a second expanding portion arranged at the back of the first expanding portion and adjoining to the first expanding portion, and at least one of the first expanding portion and the second expanding portion is replaceable independently.

13. The beam shaping assembly for neutron capture therapy according to claim 11, wherein the reflector at least comprises a supplementary reflecting portion surrounding the expanding portion.

14. The beam shaping assembly for neutron capture therapy according to claim 13, wherein both of the supplementary reflecting portion and the expanding portion are replaceable to adjust the epithermal neutron energies.

15. The beam shaping assembly for neutron capture therapy according to claim 14, wherein the supplementary reflecting portion and the expanding portion are moved into the beam shaping assembly through a guide slot arranged on the reflector to adjust the epithermal neutron energies.

16. The beam shaping assembly for neutron capture therapy according to claim 14, wherein the supplementary reflecting portion and the reflector surrounding the base portion co-reflect deflected neutrons.

17. A beam shaping assembly for neutron capture therapy comprising:
    a beam inlet;

a target, wherein the target has nuclear reaction with an incident proton beam from the beam inlet to produce neutrons;

a moderator adjoining to the target, wherein the neutrons are moderated by the moderator to epithermal neutron energies, the moderator comprises at least a expanding portion, the expanding portion is replaceable independently without changing the whole moderator;

a reflector surrounding the moderator, wherein the reflector leads deflected neutrons back to enhance epithermal neutron beam intensity; and a beam outlet.

18. The beam shaping assembly for neutron capture therapy according to claim 17, wherein the expanding portion at least comprises a first expanding portion adjoining to the target and a second expanding portion, the first expanding portion is near the target, the second expanding portion arranged at the back of the first expanding portion and adjoining to the first expanding portion, and at least one of the first expanding portion and the second expanding portion is replaceable independently.

19. The beam shaping assembly for neutron capture therapy according to claim 18, wherein the moderator comprises a base portion fixed to the target, and the first expending portion is disposed on the back of the base portion.

20. The beam shaping assembly for neutron capture therapy according to claim 17, wherein the expanding portion is made of at least one of Al, Pb, Ti, Bi, C, $D_2O$, $AlF_3$, $CaF_2$, $Li_2CO_3$, $MgF_2$ and $Al_2O_3$.

\* \* \* \* \*